United States Patent
Bera et al.

(10) Patent No.: US 10,646,414 B2
(45) Date of Patent: May 12, 2020

(54) PERSONAL CLEANSING COMPOSITION

(71) Applicant: Conopco, Inc., Englewood Cliffs, NJ (US)

(72) Inventors: Arijit Bera, South Parganas (IN); Kelvin Brian Dickinson, Wirral (GB); Richa Sureshchand Goyal, Bangalore (IN); Joseph Muscat, Warrington (GB); Paul Stephen Whitehead, Birkenhead (GB); Sally Elizabeth Wood, Warrington (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 206 days.

(21) Appl. No.: 15/571,564

(22) PCT Filed: May 3, 2016

(86) PCT No.: PCT/EP2016/059923
§ 371 (c)(1),
(2) Date: Nov. 3, 2017

(87) PCT Pub. No.: WO2016/180685
PCT Pub. Date: Nov. 17, 2016

(65) Prior Publication Data
US 2019/0117525 A1 Apr. 25, 2019

(30) Foreign Application Priority Data
May 11, 2015 (EP) ..................... 15167118

(51) Int. Cl.
| | |
|---|---|
| *A61K 8/18* | (2006.01) |
| *A61K 8/02* | (2006.01) |
| *A61K 8/31* | (2006.01) |
| *A61Q 5/02* | (2006.01) |
| *A61K 8/92* | (2006.01) |
| *A61Q 19/10* | (2006.01) |
| *A61K 8/06* | (2006.01) |
| *A61K 8/19* | (2006.01) |
| *A61K 8/365* | (2006.01) |
| *A61K 8/46* | (2006.01) |
| *A61K 8/89* | (2006.01) |
| *A61Q 5/12* | (2006.01) |

(52) U.S. Cl.
CPC ............ *A61K 8/0291* (2013.01); *A61K 8/062* (2013.01); *A61K 8/19* (2013.01); *A61K 8/31* (2013.01); *A61K 8/365* (2013.01); *A61K 8/463* (2013.01); *A61K 8/89* (2013.01); *A61K 8/92* (2013.01); *A61Q 5/02* (2013.01); *A61Q 5/12* (2013.01); *A61Q 19/10* (2013.01)

(58) Field of Classification Search
CPC ........ A61K 8/0291; A61K 8/062; A61K 8/19; A61K 8/31; A61K 8/365; A61K 8/463; A61K 8/89; A61Q 5/02; A61Q 5/12; A61Q 19/10
See application file for complete search history.

(56) References Cited

U.S. PATENT DOCUMENTS

| | | | | |
|---|---|---|---|---|
| 5,308,526 A | * | 5/1994 | Dias ................. | A61K 8/31 510/158 |
| 5,661,189 A | * | 8/1997 | Grieveson ............ | A61K 8/37 514/784 |
| 5,854,293 A | * | 12/1998 | Glenn, Jr. ............ | A61K 8/11 510/152 |
| 5,965,500 A | * | 10/1999 | Puvvada .............. | A61K 8/345 510/130 |
| 6,001,344 A | * | 12/1999 | Villa ................... | A61K 8/442 424/78.02 |
| 7,084,104 B2 | * | 8/2006 | Martin ................ | A61K 8/442 424/401 |
| 7,098,180 B2 | * | 8/2006 | Ganopolsky ......... | A61K 8/442 424/401 |

(Continued)

FOREIGN PATENT DOCUMENTS

| | | |
|---|---|---|
| JP | 3003503333 | 1/2003 |
| JP | 2015074606 | 4/2015 |

(Continued)

OTHER PUBLICATIONS

Cecile A. Dreiss, Wormlike micelles: where do we stand? Recent developments, linear rheology and scattering techniques, Soft Matter, 2007, pp. 956-970; XP055116849, vol. 3, No. 8.
Hashizaki et al., New Lecithin Organogels from Lecithin/ Polyglycerol/ Oil Systems, Journal of Oleo Science, 2012, pp. 267-275, 61 (5).
IPRP2 in PCTEP2016059923, Mar. 3, 2017.
Search Report and Written Opinion in EP15167118, dated Feb. 11, 2015.
Search Report and Written Opinion in PCTEP2016059923, dated Jul. 5, 2016.

*Primary Examiner* — Nicholas D Lucchesi
(74) *Attorney, Agent, or Firm* — Foley & Lardner LLP

(57) ABSTRACT

The invention provides a personal cleansing composition having an aqueous continuous phase including cleansing surfactant and a solubilised hydrocarbon oil having a kinematic viscosity of 1 to 35 cSt at 40° C. and a specific gravity of 0.76 to 0.87 at 25° C.; in which the hydrocarbon oil is solubilised in wormlike micelles in the aqueous continuous phase by means of a linker molecule and an inorganic electrolyte; in which the linker molecule is selected from one or more compounds of formula: $R(X)_n$, in which R is a $C_6$ to $C_{14}$ mono-, di- or trivalent saturated aliphatic or an aromatic hydrocarbyl group, n is 1 to 3 and each X is independently selected from —OH and —COOH; and in which the level of hydrocarbon oil in the composition ranges from 0.8 to 1.5% by weight based on the total weight of the composition.

18 Claims, No Drawings

(56) References Cited

U.S. PATENT DOCUMENTS

| | | | |
|---|---|---|---|
| 7,129,201 B2* | 10/2006 | Yang | A61K 8/06 510/417 |
| 8,772,212 B2* | 7/2014 | Restrepo | A61K 8/0291 510/159 |
| 9,610,239 B2* | 4/2017 | Feng | A61K 8/4993 |
| 2002/0034489 A1* | 3/2002 | Wiegland | A61K 8/02 424/70.24 |
| 2002/0039564 A1* | 4/2002 | Dickinson | A61K 8/31 424/70.1 |
| 2004/0116539 A1* | 6/2004 | Biercevicz | B01F 3/04985 516/21 |
| 2004/0121925 A1* | 6/2004 | Harmalker | A61K 8/11 510/119 |
| 2004/0136943 A1* | 7/2004 | Tomokuni | A61K 8/342 424/70.31 |
| 2006/0246022 A1 | 11/2006 | Bureiko et al. | |
| 2006/0252662 A1* | 11/2006 | Soffin | A61K 8/03 510/130 |
| 2007/0135319 A1* | 6/2007 | Wei | A61K 8/03 510/101 |
| 2008/0311062 A1* | 12/2008 | Dickinson | A61K 8/06 424/70.1 |
| 2009/0098078 A1* | 4/2009 | Dickinson | A61K 8/064 424/70.11 |
| 2010/0015077 A1* | 1/2010 | Adams | A61K 8/368 424/70.11 |
| 2010/0035783 A1 | 2/2010 | Restrepo et al. | |
| 2010/0215595 A1* | 8/2010 | Kennan | A61K 8/042 424/59 |
| 2010/0291165 A1* | 11/2010 | Glenn, Jr. | A61K 8/046 424/401 |
| 2011/0177019 A1* | 7/2011 | Dickinson | A61K 8/042 424/70.15 |
| 2014/0308229 A1* | 10/2014 | Bouzeloc | C08K 5/06 424/70.122 |
| 2015/0216790 A1* | 8/2015 | Feng | A61K 8/4993 424/401 |
| 2017/0020793 A1* | 1/2017 | Avery | A61K 8/31 |
| 2018/0098923 A1* | 4/2018 | Hutton, III | A61K 8/042 |

FOREIGN PATENT DOCUMENTS

| | | |
|---|---|---|
| WO | WO0100151 | 1/2001 |
| WO | WO2015082241 | 6/2015 |
| WO | WO2019130990 | 7/2019 |

* cited by examiner

PERSONAL CLEANSING COMPOSITION

FIELD OF THE INVENTION

The present invention relates to personal cleansing compositions such as liquid soaps, body washes and shampoos.

BACKGROUND And PRIOR ART

In order to provide skin or hair conditioning benefits in a cleansing base such as a liquid soap, body wash or shampoo, it has been proposed to include beneficial oils. Mineral oil is one such example. It acts as a non-greasy lubricant, helps in detangling hair, and can form a barrier on the hair surface to protect the cuticle and create a smooth, fly-away free look.

Since shampoo is a "rinse-off" product, the level of mineral oil deposited on hair can be low. However, incorporation of higher levels of oil into the product is not always possible since it may lower the viscosity and disrupt the product microstructure, resulting in undesirable phase separation.

The present invention addresses this problem.

SUMMARY OF THE INVENTION

The present invention provides a personal cleansing composition having an aqueous continuous phase including cleansing surfactant and a solubilised hydrocarbon oil having a kinematic viscosity of 1 to 35 cS ($mm^2 \cdot s^{-1}$) at 40° C. and a specific gravity of 0.76 to 0.87 at 25° C.;
in which the hydrocarbon oil is solubilised in wormlike micelles in the aqueous continuous phase via the incorporation of at least one inorganic electrolyte and at least one linker molecule which is selected from compounds of general formula (I):

$$R(X)_n \qquad (I)$$

in which R is an aromatic hydrocarbyl ring having from 6 to 10 carbon atoms or a mono-, di- or trivalent saturated aliphatic hydrocarbyl chain having from 3 to 14 carbon atoms; n is 1 to 3 and each X is independently selected from —OH and —COOH;
and in which the level of hydrocarbon oil in the composition ranges from 0.8 to 1.5% by weight based on the total weight of the composition.

DETAILED DESCRIPTION AND PREFERRED EMBODIMENTS

By "aqueous continuous phase" is meant a continuous phase which has water as its basis.

Suitably, the composition of the invention will comprise from about 50 to about 90%, preferably from about 55 to about 85%, more preferably from about 60 to about 85%, most preferably from about 65 to about 83% water (by weight based on the total weight of the composition).

The cleansing surfactant may suitably be selected from one or more anionic surfactants.

Typical anionic surfactants for use as cleansing surfactants in the invention include those surface active agents which contain an organic hydrophobic group with from 8 to 14 carbon atoms, preferably from 10 to 14 carbon atoms in their molecular structure; and at least one water-solubilising group which is preferably selected from sulphate, sulphonate, sarcosinate and isethionate.

Specific examples of such anionic surfactants include ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyl sarcosinate, lauryl sarcosine, ammonium cocoyl sulphate, ammonium lauroyl sulphate, sodium cocoyl sulphate, sodium lauryl sulphate, potassium cocoyl sulphate, potassium lauryl sulphate, monoethanolamine cocoyl sulphate, monoethanolamine lauryl sulphate, sodium tridecyl benzene sulphonate, sodium dodecyl benzene sulphonate, sodium cocoyl isethionate and mixtures thereof.

A preferred class of anionic surfactants for use as cleansing surfactants in the invention are alkyl ether sulphates of general formula:

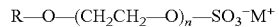

$$R\text{—}O\text{—}(CH_2CH_2\text{—}O)_n\text{—}SO_3^-M^+$$

in which R is a straight or branched chain alkyl group having 10 to 14 carbon atoms, n is a number that represents the average degree of ethoxylation and ranges from 1 to 5, preferably from 2 to 3.5, and M is a alkali metal, ammonium or alkanolammonium cation, preferably sodium, potassium, monoethanolammonium or triethanolammonium, or a mixture thereof.

Specific examples of such preferred anionic surfactants include the sodium, potassium, ammonium or ethanolamine salts of $C_{10}$ to $C_{12}$ alkyl sulphates and $C_{10}$ to $C_{12}$ alkyl ether sulphates (for example sodium lauryl ether sulphate), Mixtures of any of the above described materials may also be used.

In a typical composition according to the invention the level of cleansing surfactant will generally range from 5 to 26% (by weight based on the total weight of the composition).

The composition of the invention includes a solubilised hydrocarbon oil having a kinematic viscosity of 1 to 35 cS ($mm^2 \cdot s^{-1}$) at 40° C. and a specific gravity of 0.76 to 0.87 at 25° C.

Suitable hydrocarbon oils in the context of the present invention include saturated, non-polar straight or branched-chain aliphatic or alicyclic hydrocarbons having from about 10 to about 50 carbon atoms, and mixtures thereof. A preferred hydrocarbon oil in the context of the present invention is light mineral oil. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons, in which the number of carbon atoms per hydrocarbon molecule generally ranges from $C_{10}$ to $C_{40}$.

The mineral oil may be characterised in terms of its viscosity, where light mineral oil is less viscous than heavy mineral oil. A suitable light mineral oil will generally have a kinematic viscosity of 3.9 to 5.0 cS ($mm^2 \cdot s^{-1}$) at 40° C. and a specific gravity of 0.810 to 0.830 at 25° C. Such materials are commercially available under the brand name Lytol®.

The level of solubilised hydrocarbon oil (as defined above) in compositions of the invention preferably ranges from about 0.8 to about 1.2%, more preferably from about 0.9 to about 1.1%, ideally about 1% by weight based on the total weight of the composition.

The hydrocarbon oil is solubilised in wormlike micelles in the aqueous continuous phase.

"Wormlike micelles" in the context of this invention are elongated and flexible aggregates formed by the self-assembly of surfactant molecules in water. Above a threshold concentration, wormlike micelles entangle into a transient network, reminiscent of polymer solutions, and display viscoelastic properties. However, unlike a covalently bonded polymer backbone, the micelles are in a state of thermodynamic equilibrium with the solvent and are perpetually broken and reformed under Brownian fluctuations. This leads to a broad and dynamic distribution of micelle lengths which can change under an imposed shear or extensional flow.

Wormlike micelles can be fully described by a number of structural parameters, which cover a broad range of length-scales. The overall length of the micelles is referred to as the contour length L and varies between a few (e.g. about 1 to 10) nanometers up to a few (e.g. about 1 or 2) microns. Cryo-TEM provides a direct visualization of the micelles and can be used to estimate the contour length, while light and neutron scattering give a more accurate determination. Radii of wormlike micelles are typically a few (e.g. about 1 to 10) nm. Another key structural parameter in the description of wormlike micelles is the persistence length $l_p$, the length over which the micelles are considered rigid. Although wormlike micelles can be extremely flexible and micrometres long, their large cross-section implies that on smaller length-scales (of order $l_p$) they act as rigid rods. Techniques such as rheology, light and neutron scattering and flow birefringence have been employed to estimate $l_p$, as well as simulations. Experimentally, persistence lengths from about 10 to about 40 nm have been reported in neutral systems. For charged wormlike micelles, the persistence length varies significantly with surfactant structure, counterion and salt concentration, but is typically a few tens of nanometers (e.g about 30 to about 100 nm).

The hydrocarbon oil is solubilised in wormlike micelles in the aqueous continuous phase via the incorporation of at least one inorganic electrolyte and at least one linker molecule as defined above.

"Linker molecules" in the context of this invention are chemical additives used in surfactant systems that enhance the surfactant-oil or surfactant-water interactions. Lipophilic linkers segregate near the oil side of the interface close to the tails of the surfactants. The presence of the lipophilic linker extends the impact of the surfactant deeper into the oil phase and may promote additional orientation of the oil molecules. Hydrophilic linkers are surfactant-like molecules that coadsorb with the surfactant at the oil/water interface, but have a minimal interaction with the oil molecules. The adsorption of the hydrophilic linker at the oil/water interface increases the total interfacial area.

R in general formula (I) above is preferably an aromatic hydrocarbyl ring having 6 carbon atoms or a mono-, di- or trivalent linear saturated aliphatic hydrocarbyl chain having from 3 to 12 carbon atoms.

Examples of preferred linker molecules for use in the invention include phthalic acid, citric acid, mono- or dicarboxylic acids of formula Y—$CH_2(CH_2)_m$—COOH, in which Y is selected from —H and —COOH and m is an integer ranging from 4 to 12, more preferably from 6 to 10 (for example: caprylic. acid, lauric acid and azelaic acid); and diols of formula HO—$CH_2(CH_2)_m CH_2$—OH, where m is as defined above (for example: 1,12-dodecanediol).

Mixtures of any of the above described materials may also be suitable.

The level of linker molecule of general formula (I) above in compositions of the invention preferably ranges from about 0.01 to about 1%, more preferably from about 0.02 to about 0.5%, most preferably from about 0.05 to about 0.15% by weight based on the total weight of the composition.

The weight ratio of solubilised hydrocarbon oil (as defined above) to linker molecule of general formula (I) above in compositions of the invention generally ranges from about 15:1 to about 1:1, preferably from about 12:1 to about 6:1, more preferably from about 10:1 to about 8:1.

The composition of the invention includes at least one inorganic electrolyte. The inorganic electrolyte is used to assist in the solubilisation of the hydrocarbon oil and to provide viscosity to the composition.

The viscosity of the composition suitably ranges from 6,000 to 10,000 mPa·s, preferably from 7,000 to 9,000 mPa·s, more preferably from 7,500 to 8,500 mPa·s when measured using a Brookfield V2 viscometer (spindle RTV5, 1 minute, 20 rpm) at 30° C.

Suitable inorganic electrolytes include metal chlorides (such as sodium chloride, potassium chloride, calcium chloride, magnesium chloride, zinc chloride, ferric chloride and aluminium chloride) and metal sulphates (such as sodium sulphate and magnesium sulphate).

Examples of preferred inorganic electrolytes for use in the invention include sodium chloride, potassium chloride, magnesium sulphate and mixtures thereof.

Mixtures of any of the above described materials may also be suitable.

The level of inorganic electrolyte in compositions of the invention generally ranges from about 1 to about 25%, preferably from about 2 to about 20%, more preferably from about 3 to about 15% (by total weight inorganic electrolyte based on the total weight of the composition).

The composition of the invention generally includes additional hair and/or skin conditioning ingredients, such as in particular silicones.

Silicone is typically present in the composition as emulsified droplets having a mean droplet diameter (D3,2) of 4 micrometres or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

Preferably the silicone is non-volatile, meaning that it has a vapour pressure of less than 1000 Pa at 25° C.

Suitable silicones for use in the invention include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

All molecular weights as used herein are weight average molecular weights, unless otherwise specified.

Suitable silicones preferably have a kinematic viscosity of greater than 50,000 cS ($mm^2 \cdot s^{-1}$) and more preferably a kinematic viscosity of greater than 500,000 cS ($mm^2 \cdot s^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in compositions of the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a mean droplet diameter (D3,2) of less than 0.15 micrometers are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

The amount of silicone in compositions of the invention may suitably range from 0.05 to 10%, preferably from 0.2 to 8% (by total weight silicone based on the total weight of the composition).

The composition of the invention preferably includes one or more cationic polymers. Such polymers may enhance the delivery of conditioning agents and thereby improve the conditioning benefits obtained.

Cationic polymers typically contain cationic nitrogen-containing groups such as quaternary ammonium or protonated amino groups. The cationic protonated amines can be primary, secondary, or tertiary amines (preferably secondary or tertiary). The average molecular weight of the cationic polymer is preferably from 5,000 to 10 million. The cationic polymer preferably has a cationic charge density of from 0.2 meq/gm to 7 meq/gm.

The term "cationic charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain.

The cationic nitrogen-containing moiety of the cationic polymer is generally present as a substituent on all, or more typically on some, of the repeat units thereof. The cationic polymer may be a homo-polymer or co-polymer of quaternary ammonium or cationic amine-substituted repeat units, optionally in combination with non-cationic repeat units. Particularly suitable cationic polymers for use in the invention include polysaccharide polymers, such as cationic cellulose derivatives, cationic starch derivatives, and cationic guar gum derivatives.

A particularly suitable type of cationic polysaccharide polymer that can be used is a cationic guar gum derivative, such as guar hydroxypropyltrimethylammonium chloride. (commercially available from Rhodia® in their JAGUAR® trademark series). Examples of such materials are JAGUAR® C13S, JAGUAR® C14, JAGUAR® C15 and JAGUAR® C17.

Mixtures of any of the above described cationic polymers may also be used.

When included, the total level of cationic polymer in the composition is preferably from 0.05% to 2% and more preferably from 0.1 to 0.5% by weight based on the total weight of the composition.

The composition of the invention preferably includes one or more amphoteric surfactants. Suitable amphoteric surfactants are betaines, such as those having the general formula $R(CH_3)_2N^+CH_2COO^-$, where R is an alkyl or alkylamido-alkyl group, the alkyl group preferably having 10 to 16 carbon atoms. Particularly suitable betaines are oleyl betaine, caprylamidopropyl betaine, lauramidopropyl betaine, isostearylamidopropyl betaine, and cocoamidopropyl betaine.

When included, the total level of amphoteric surfactant is generally from 0.1% to 20%, preferably from 1% to 10%, more preferably from 1% to 5% by weight based on the total weight of the composition.

The composition of the invention preferably includes one or more suspending agents. Suitable suspending agents include polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives.

Mixtures of any of the above suspending agents may be used. Preferred is a mixture of cross-linked polymer of acrylic acid and crystalline long chain acyl derivative.

When included, the total level of suspending agent is generally 0.1 to 10%, preferably from 0.5 to 6%, more preferably from 0.9 to 4% by weight based on the total weight of the composition.

A composition of the invention may contain further optional ingredients to enhance performance and/or consumer acceptability. Examples of such ingredients include fragrance, dyes and pigments, pH adjusting agents and preservatives or antimicrobials. Each of these ingredients will be present in an amount effective to accomplish its purpose. Generally these optional ingredients are included individually at a level of up to 5% by weight based on the total weight of the composition.

The composition of the invention is primarily intended for topical application to the body, preferably the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples, in which all percentages quoted are by weight based on total weight unless otherwise stated.

EXAMPLES

Hair cleansing shampoo formulations were prepared, having ingredients as shown in Table 1. Example 1 represents a formulation according to the invention. Examples A, B and C represent comparative examples (not according to the invention).

TABLE 1

| Ingredient | Example A (% w/w) | Example B (% w/w) | Example 1 (% w/w) | Example C (% w/w) |
|---|---|---|---|---|
| Sodium laureth sulphate (1EO) | 12 | 12 | 12 | 12 |
| Cocamidopropyl betaine | 1.6 | 1.6 | 1.6 | 1.6 |
| Guar hydroxypropyltrimonium chloride | 0.2 | 0.2 | 0.2 | 0.2 |
| Dimethiconol* | 2 | 2 | 2 | 2 |
| Carbomer | 0.4 | 0.4 | 0.4 | 0.4 |
| Ethylene glycol distearate | 2.5 | 2.5 | 2.5 | 2.5 |
| Mica | 0.2 | 0.2 | 0.2 | 0.2 |
| Disodium EDTA | 0.1 | 0.1 | 0.1 | 0.1 |
| Citric acid | 0.1 | 0.1 | 0.1 | 0.1 |

TABLE 1-continued

| Ingredient | Example A (% w/w) | Example B (% w/w) | Example 1 (% w/w) | Example C (% w/w) |
|---|---|---|---|---|
| Sodium hydroxide | 0.15 | 0.15 | 0.15 | 0.15 |
| Sodium chloride | 0.5 | 2.0 | 3.2 | 4.4 |
| Octanoic acid | 0 | 0.05 | 0.1 | 0.2 |
| Lytol ® mineral oil | 0 | 0.45 | 0.9 | 1.8 |
| Water, perfume, preservatives | to 100% | to 100% | to 100% | to 100% |

*Emulsion of dimethiconol with anionic emulsifier, average particle size <1 micron (ex Dow Corning)

Viscosity

The viscosity of the formulations was measured by using a Brookfield V2 viscometer (spindle RTV5, 1 minute, 20 rpm) at 30° C. The results are shown in Table 2.

TABLE 2

| | Viscosity (mPa · s) |
|---|---|
| Example A | 5380 |
| Example B | 7960 |
| Example 1 | 7800 |
| Example C | 3800 |

Measurement of Silicone Deposition 0.25 g test formulation is applied to 2.5 g of wet hair switches. The formulation is massaged on hair for 30 seconds followed by rinsing with warm water for 30 seconds. This treatment is repeated once. Silicone deposition was measured by X-ray Fluorescence (XRF). Five hair switches were measured for each formulation.

The average of measured silicone deposition is shown in Table 3.

TABLE 3

| Silicone deposition | Example A | Example B | Example 1 |
|---|---|---|---|
| Mean/ppm | 1062 | 1367 | 1420 |
| Standard deviation | 120 | 118 | 143 |

The results show that Example 1 demonstrates superior silicone deposition without any significant loss of shampoo viscosity (as is observed in the case of Example C).

The invention claimed is:

1. A personal cleansing composition having an aqueous continuous phase including cleansing surfactant and a solubilised hydrocarbon oil; the hydrocarbon oil being selected from saturated, non-polar straight or branched-chain aliphatic or alicyclic hydrocarbons having from about 10 to about 50 carbon atoms, and mixtures thereof; and the hydrocarbon oil having a kinematic viscosity of 1 to 35 cS (mm$^2 \cdot$s$^{-1}$) at 40° C. and a specific gravity of 0.76 to 0.87 at 25° C.;

in which the hydrocarbon oil is solubilised in micelles in the aqueous continuous phase via the incorporation of at least one inorganic electrolyte and at least one linker molecule which is selected from compounds of general formula (I):

$$R(X)_n \quad (I)$$

in which R is an aromatic hydrocarbyl ring having from 6 to 10 carbon atoms or a mono-, di- or trivalent saturated aliphatic hydrocarbyl chain having from 3 to 14 carbon atoms; n is 1 to 3 and each X is independently selected from —OH and —COOH;

and in which the level of hydrocarbon oil in the composition ranges from 0.9 to 1.1% by weight based on the total weight of the composition;

and in which the composition also includes emulsified droplets of silicone having a mean droplet diameter (D3,2) of 0.25 micrometre or less, in an amount ranging from 0.2 to 8% by total weight silicone based on the total weight of the composition.

2. A composition according to claim 1, in which the hydrocarbon oil is light mineral oil having a kinematic viscosity of 3.9 to 5.0 cS (mm$^2 \cdot$s$^1$) at 40° C. and a specific gravity of 0.810 to 0.830 at 25° C.

3. A composition according to claim 1, in which R in general formula (I) is an aromatic hydrocarbyl ring having 6 carbon atoms or a mono-, di- or trivalent linear saturated aliphatic hydrocarbyl chain having from 3 to 12 carbon atoms.

4. A composition according to claim 3, in which the linker molecule is selected from phthalic acid, citric acid, caprylic acid, lauric acid, azelaic acid, 1,12-dodecanediol; and mixtures thereof.

5. A composition according to claim 1, wherein the micelle structures are elongated and flexible.

6. A composition according to claim 1, wherein the micelle structures have a length between 1 nm and 2 μm.

7. A composition according to claim 1, wherein the micelle structures have a radii between 1 nm and 10 nm.

8. A composition according to claim 1, wherein the viscosity is between 6,000 to 10,000 mPa·s when measured using a Brookfield V2 viscometer with spindle RTV5 for 1 minute at 20 rpm and 30° C.

9. A composition according to claim 1, wherein the electrolyte is one of a metal chloride and a metal sulphate.

10. A composition according to claim 1, wherein the electrolyte is one of sodium chloride, potassium chloride, magnesium sulphate and a mixture thereof.

11. A composition according to claim 1, wherein the electrolyte weight percent ranges between 1% and 25%.

12. A composition according to claim 1, wherein the silicone has a weight average molecular weight greater than 100,000.

13. A composition according to claim 1, wherein the silicone is selected from the group consisting of polydimethylsiloxane, polydimethylsiloxane with hydroxyl end groups, and amino-functional polydimethylsiloxanes.

14. A composition according to claim 1, further comprising a cationic polymer.

15. A composition according to claim 14, wherein the weight average molecular weight of the cationic polymer is between 5,000 and 10 million.

16. A composition according to claim 14, wherein the cationic charge density of the cationic polymer is between 0.2 meq/gm and 7 meq/gm.

17. A composition according to claim 14, wherein the weight percent of the cationic polymer is between 0.05% and 2%.

18. A method of cleansing and conditioning hair, comprising the following sequential steps:

(i) topically applying a composition according to claim 1 to the hair;
    (ii) massaging the composition into the hair and scalp;
    (iii) rinsing the composition off the hair and scalp with water, and
    (iv) drying the hair.